(12) United States Patent
Hoenig

(10) Patent No.: US 6,770,060 B2
(45) Date of Patent: Aug. 3, 2004

(54) PERSONAL HYGIENE SYSTEM

(76) Inventor: Timothy Hoenig, P.O. Box 7261, South Lake Tahoe, CA (US) 96158

( * ) Notice: Subject to any disclaimer, the term of this patent is extended or adjusted under 35 U.S.C. 154(b) by 280 days.

(21) Appl. No.: 09/952,473

(22) Filed: Sep. 13, 2001

(65) Prior Publication Data

US 2003/0055399 A1 Mar. 20, 2003

(51) Int. Cl.[7] ............................................. A61M 31/00
(52) U.S. Cl. ...................................... 604/279; 604/515
(58) Field of Search .............................. 604/19, 28, 36, 604/39, 93.01, 181, 187, 257, 264, 275, 279, 902, 514, 515; 4/420.1–420.5, 443–448, 559, 567, 605, 615, 661

(56) References Cited

U.S. PATENT DOCUMENTS

| | | |
|---|---|---|
| 3,921,635 A | 11/1975 | Gauthier |
| 3,965,899 A | 6/1976 | Murray et al. |
| 4,642,100 A | 2/1987 | Kabbaby |
| 4,701,164 A | 10/1987 | Cassou et al. |
| 4,950,231 A | 8/1990 | Liu |
| 5,102,387 A | 4/1992 | Jorde |
| 5,241,714 A * | 9/1993 | Barry ............................ 4/605 |
| 5,304,116 A * | 4/1994 | Cornelius .................... 604/39 |
| 5,685,028 A | 11/1997 | Miller et al. |
| 5,695,481 A | 12/1997 | Heinzelman et al. |
| 5,823,441 A * | 10/1998 | Nicholson ................... 239/317 |
| 6,190,365 B1 | 2/2001 | Abbott et al. |
| 6,206,862 B1 | 3/2001 | Giamanco et al. |
| 6,235,008 B1 | 5/2001 | Heinzelman et al. |

* cited by examiner

Primary Examiner—Brian L. Casler
Assistant Examiner—Michael M. Thompson
(74) Attorney, Agent, or Firm—Townsend and Townsend and Crew LLP

(57) ABSTRACT

Devices and methods for personal hygiene. The devices of the present invention include a connector that can connect to an output of a shower head to deliver a flow of fluid through a fluid conduit to an applicator for delivery of a fluid flow and/or cleaning agent to a target area, such as the vagina. Optionally, a valve assembly and reservoir for medicant or a cleaning solution can be disposed adjacent the applicator.

12 Claims, 7 Drawing Sheets

PERSONAL HYGIENE SYSTEM

BACKGROUND OF THE INVENTION

The present invention is generally related to a personal hygiene system. More specifically, the present invention is related to a shower douching system.

Douching is a form of feminine hygiene that uses chemicals that do not detrimentally reduce the amount of natural enzymes present in the female reproductive tract. In some religious groups, douching has sometimes been used as a form of birth control to wash at least some of the sperm from the vaginal canal after sexual intercourse.

There are a variety of personal hygiene systems or douching devices that are available on the market. Such devices generally take the form of a stand alone douching device or a hand held shower douching device. While the conventional douching apparatuses have been successful, each of the conventional solutions have undesirable drawbacks. For example, douching systems that divert a portion of the water flow away from the shower head to the douching device typically require a separate valve that must be manually attached between the shower head and the water source. Such devices are often cumbersome, difficult to mount to the water supply, and are not aesthetically pleasing since such plumbing and douching devices are often permanently attached to the shower head. In regards to the stand alone devices, such stand alone devices are often costly, large and unsightly and often cannot be added to an existing structure without extensive remodeling or re-plumbing.

Therefore, what are needed are personal hygiene systems that would be easily attachable to any pressurized water system with potable water. It is further desirable to provide a system that can simply be attached and detached from a conventional shower head. It would further be desirable if such a system did not require a complex network of pipes and valves that require the use of specialized tools. It would be preferred if such a system was not permanently attached to fixed plumbing and could be moved out of sight and stored so as to minimize the user's embarrassment from untimely questions from children.

DESCRIPTION OF THE BACKGROUND ART

U.S. Pat. Nos. 4,950,231 and 5,685,028 describe stand alone personal hygiene systems. U.S. Pat. Nos. 6,206,862, 5,241,714, and 4,642,100 describe a shower douching apparatus that includes a bypass system that diverts a flow of water away from the shower head. U.S. Pat. Nos. 5,102,387 and 3,921,635 describe shower douching apparatuses that attach to a hand held shower head.

BRIEF SUMMARY OF THE INVENTION

The present invention provides a personal hygiene system that is readily attachable and detachable from a conventional wall mounted shower head so as to allow a user to douche in the shower. Advantageously, the devices of the present invention allow the user to adjust the temperature and flow rate of the fluid flow through the douching device.

The present invention typically includes a "quick-connect" connector or knob that can attach and detach from an output of a shower rose or shower head. In exemplary embodiments the present invention takes advantage of an existing threaded opening that is present in many conventional shower heads. The existing gasket and spray adjustment component is removed and the quick connect can be threadedly attached so as to direct at least a portion of the water flow from the shower head into the personal hygiene systems of the present invention.

Unlike conventional shower douching systems that require additional plumbing and complex diverting assemblies, users can simply attach and detach the quick-connect connector to the output face of the shower head so as to take the water flow that normally flows from the shower head and divert some or all of the water into the douching or personal hygiene systems of the present invention. Such systems allow for simple and easy attachment and detachment with an existing shower head, without the need to disassemble the shower head.

Because of the simplicity of the present invention, the user may shower only, douche only, or shower and douche at the same time. Advantageously, to change between the various modes, the user need only tighten or loosen the connector on the shower head.

In a showering mode, the user can leave the connector or knob connected to the shower head, or alternatively can completely remove the connector and leave the existing gasket and spray adjustment component in the shower head. In such shower-only methods in which the connector is left on the shower head, the user can turn on the water and adjust the flow and temperature to a desired level. To shower, water can be directed only through the connector or it can be directed around and through the connector. To allow water to flow around and through the connector, the user can manually loosen the connector from the shower head so as to allow water to flow around the connector. If the user wishes to have water flow only through the connector, the user can tighten the connection between the connector and shower head, until water flows only through the connector.

If the user wishes to shower and douche concurrently, after the user has adjusted the temperature and flow to a desirable temperature and flow rate, the user can then connect a fluid conduit to the connector to direct the water that flows through the connector through the fluid conduit to a douching applicator. Similar to above, by adjusting the quick connect (by tightening or loosening the connector), the user can adjust the amount of water that flows around and into the connector and into the shower environment.

If the user desires only to douche, the user can completely tighten the quick connect knob and attach the fluid conduit to the connector so as to divert 100% of the water into the connector and douching system. Thus, if the user wishes to stay dry and only douche, the user can connect and/or tighten the quick connect to the shower head, attach the fluid conduit, and divert 100% of the water through the douching system. This would allow the user to stay completely dry from the waist up, if not entirely dry. Optionally, in some embodiments, the fluid conduit can be of a length that allows the user to douche while on the commode.

In one particular aspect, the present invention provides a personal hygiene system that is attachable to a shower head having an input interface and an output interface. The system includes a connector attachable to the output interface of the shower head so as to direct a water flow from the shower head through the connector. The fluid is directed from the connector to a flexible fluid conduit which includes an applicator for directing the fluid flow to a target portion of the user's body.

In exemplary embodiments, the connectors of the present invention are threadedly attachable to an output interface of the shower head. An exemplary shower head is manufactured by Delta Corporation.

Unlike the conventional douching shower devices, the systems of the present invention attach directly to conventional shower heads, without the need of a complex diverting system to move water away from the shower head into a separate douching system. The connectors of the present invention utilize the existing threaded opening to attach the douching system directly to the shower head.

The fluid conduit of the present invention is typically composed of a flexible rubber tubing that is capable of delivering a fluid from the connector to an applicator. Exemplary fluid conduits have an outer diameter between approximately 7/16 inches to 5/8 inches and a length of approximately three feet to fifteen feet or more. However, Applicant has found that a 3/8 inch inside diameter works well as the volume flow allows sufficient time for extraction of the applicator should the water pressure vary (i.e., a toilet flush).

The applicator of the present invention is disposed on a free end of the fluid conduit. The applicator is typically sized and shaped for insertion into a body orifice, such as the vaginal passageway of the user. As such, the applicator will typically be substantially rigid and will have a length between approximately 4 inches and 8 inches and an outer diameter between approximately 0.40 inches and 0.75 inches. The applicators can be straight, curved, or a combination thereof. It should be appreciated however, that the applicators of the present invention can have different sizes, shapes and materials without departing from the scope of the present invention.

In one exemplary embodiment, the connector includes a housing having a plurality of inlets, a passageway and a wafer shaped check valve in the passageway that is contoured to center itself within the flow of water to provide for an even water flow around the wafer shaped valve. During douching, the valve centers itself over the output conduit. The check valve may include spray holes for delivering water through the connector in both the showering and douching mode. Advantageously, such spray holes can also reduce the calcification deposits in the quick connect and fluid conduit. It should be appreciated however, that in other embodiments, other valves, such as ball valves, wafer check valves, or the like can be used in the connector to regulate the flow, and such valves may or may not have the plurality of holes in them.

In exemplary systems the connector, fluid conduit and applicator are removably coupled to each other. It is generally preferable to have the applicator removable so as to allow the user to sterilize the applicator after douching. In one particular embodiment, the fluid conduit is threadably attachable to the connector knob. In such embodiments, when the fluid conduit is attached to the connector, the threaded connection of the fluid conduit includes an end opening and radial openings for receiving the water flow from the connector. When the fluid conduit is attached to the connector, the fluid conduit lifts the wafer check valve off of its seat and allows water to flow through the check valve openings and into the conduit end opening and around the check valve and through the radial openings so as to deliver a larger flow of water from the connector through the fluid conduit.

Optionally, the douching systems of the present invention include a fluid reservoir for holding the chemical or homeopathic solutions for yeast infections, such as vinegar, baking soda or water solution. The fluid reservoir can be attached to the connector, fluid conduit or the applicator. In exemplary embodiments, the fluid reservoir is a venturi siphon chamber that is disposed between the fluid conduit and applicator. The venturi siphon chamber allows mixing of the proper rations of the solution with the water flow flowing through the system.

In exemplary vinegar mixtures, it is preferred to add 2 tablespoons of vinegar per one quart of water at a flow rate of 2.5 gallons per minute of flow or a lesser, adjusted flow rate through the shower head. Once the vinegar mixture is depleted from the reservoir, the user simply shuts of the water flow and removes the applicator.

In another aspect, the present invention provides a douching method. The method includes the step of coupling a douching system to an output of a shower head disposed on a shower wall. At least a portion of the fluid flow from the shower head is directed from the shower head through a fluid conduit to a venturi siphon chamber. A measured amount of an agent is delivered into the fluid flow and the fluid is delivered to a target area with an applicator. In exemplary methods, the douching system is directly attached to the shower head with a threaded connection.

In another aspect, the present invention provides a kit. The kit comprises a personal hygiene system including a connector having a proximal end and distal end, the proximal end being threadably connectable to a shower head, a conduit in fluid communication with the connector, and an applicator coupled to the conduit. The kit can also include instructions for use comprising threadably attaching the connector to an output interface of the shower head, attaching the fluid conduit to the fitting, and delivering a fluid through the shower head to the applicator. The kit can also include a package adapted to contain the personal hygiene assembly and the instructions for use.

The instructions for use can be disposed on a variety of types of mediums, including a computer readable medium, paper, or on the package itself. Optionally, the kit can include a powder or liquid agent and/or a reservoir for delivering the powder or liquid agent into the flow of water, as described above.

While the remaining discussion focuses on using the personal hygiene systems of the present invention as a douching device, it should be appreciated that the systems of the present invention can be used to clean or irrigate other target areas of the body. A further understanding of the nature and advantages of the invention will become apparent by reference to the remaining portions of the specification and drawings.

DETAILED DESCRIPTION OF THE INVENTION

Figure 1:
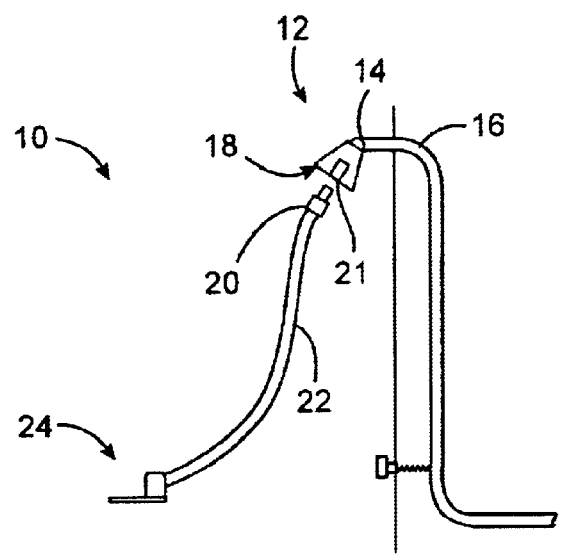
FIG. 1 is a system incorporating the present invention.

FIG. 1 illustrates a system 10 of the present invention. System includes a wall mounted shower head or shower rose 12 having an input 14 that is in fluid communication with a water source 16 (i.e. water pipe). Water flows from water source 16 through input 14 and out of an output 18 of the shower head 12. A connector 20 of the present invention is connectable to output 18 of the shower head so as to receive at least a portion of the water flow from shower head 12. Connector 20 can be coupled to a flexible fluid conduit 22 for directing the water flow to an applicator 24 to allow the user to deliver the water flow to a target area, such as the vaginal passage.

Figure 2A:
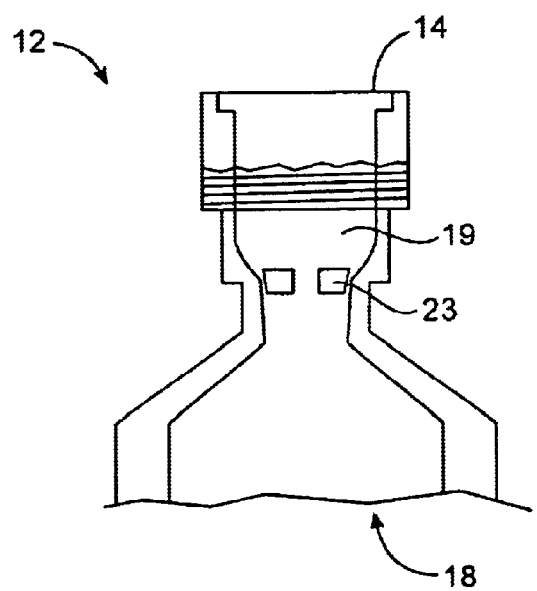
FIG. 2A is a cross sectional view of a conventional shower head.
Figure 2B:
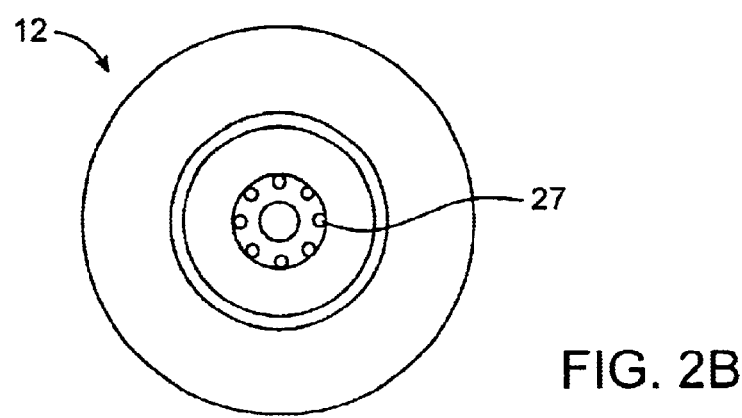
FIG. 2B is an end view of the conventional shower head of FIG. 2A.
Figure 3:
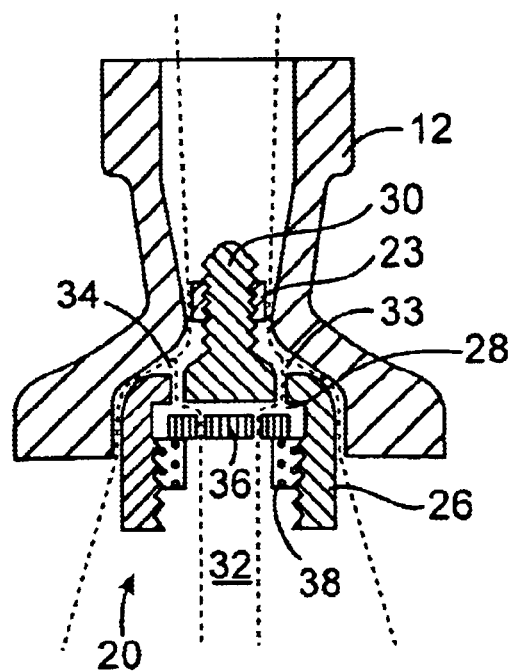
FIG. 3 is a cross sectional view of a connector threadedly attached to a shower head in the shower mode.

Systems 10 of the present invention provide a douching system that can be easily attached and detached from shower head 12 without the need for tools or additional plumbing components. In one exemplary embodiment, connector 20 is adapted to be threadedly coupled to an existing threaded opening 21 in the shower head. One exemplary shower head is manufactured by Delta Corporation. As shown in FIGS. 2A and 2B, the shower head 12 includes the inlet 14 and the output 18 that are connected via a passageway 19 (FIG. 2A). The shower head can include threads 23 for receiving connector 20 (FIG. 1). Typically, water can flow through passageway 19 and around and through openings 27. As shown in FIG. 3, to attach some connectors of the present invention, the user can remove the shower head spray adjuster and threadedly attach connector 20 to the threads 23 of shower head 12. Connector 20 can be hand tightened so as to align fluid inlets with the outlet interface 18 of shower head 12 so as to direct the fluid flow from the shower head through connector 20. It should be appreciated that in many embodiments, connector 20 can be tightened or loosened to control the amount of water flow through the connector. In exemplary embodiments, if the connector is tightened completely, 100% of the water will flow through the connector. However, if the connector 20 is loosened, a percentage of the water can be delivered around the connector and into the shower environment, while a percentage of the water can be delivered through the connector 20 to the conduit and to the applicator.

Figure 6:
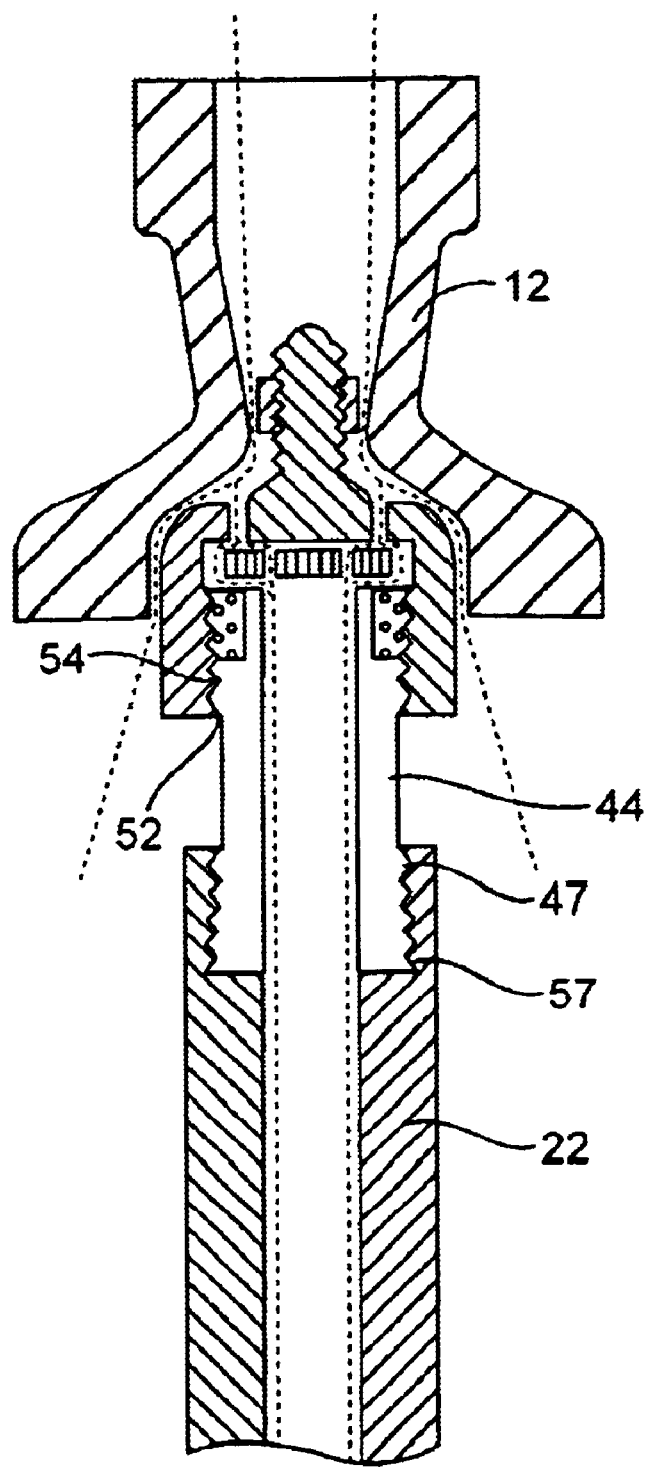
FIG. 6 is a cross sectional view of a connector threadedly attached to the shower head and fluid conduit.

FIG. 3 illustrates an exemplary quick-connect connector 20 coupled to a shower head 12. Connector 20 includes a housing 26 that defines a passageway 28 for receiving a fluid flow. Housing 26 typically has a threaded shaft 30 for threadedly attaching to threads 23 of shower head 12. Housing 26 can include at least one, and typically a plurality of inlets 33, 34 for receiving the water flow from output 18 of shower head and an output port 32 for delivering the water flow to fluid conduit 22 (FIGS. 1 and 6). Thus, water will flow from shower head 12 through inlets 33, 34 and into passageway 28 and out of outlet port 32. Passageway can also include a check valve 36, such as a contoured wafer valve, ball valve, and a valve seat 38 to control the water flow through the connector. Water flow through and around the connector is illustrated in FIG. 3 with dotted lines. As shown, in the shower mode, water can flow through shower head 12 and through and around connector 20. Water will flow through valve openings 42 (FIGS. 4 and 5) and in between shower head 12 and connector 20 when the connector is loosely attached to shower head 12. If the connector is tightly secured to shower head, the flow between the shower head 12 and connector 20 can be reduced or stopped altogether.

Figures 4, 5:
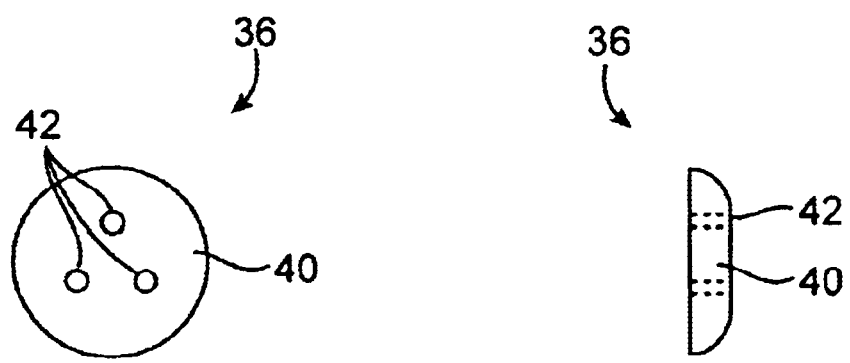
FIG. 4 is a front view of an exemplary contoured check valve of the present invention.
FIG. 5 is a side view of the contoured check valve of FIG. 4.

FIGS. 4 and 5 illustrate an exemplary contoured wafer valve 36 of the present invention. Wafer valve 36 includes a contoured body 40 having a curved body and a plurality of holes 42 that allow water to flow through. In the illustrated embodiment, the check valve includes three holes, but it should be appreciated that any number of holes can be created in the contoured wafer valve 36. The valve 36 can be positioned within passageway 28 and centered within the flow of water to provide an even water flow around the contoured valve 36 and out of connector 20. Such spray holes 42 will have a size to allow a sufficient flow of water to flow through them and a size to reduce the formation of calcification deposits in the quick connect connector 20 and fluid conduit 22.

Figure 7:
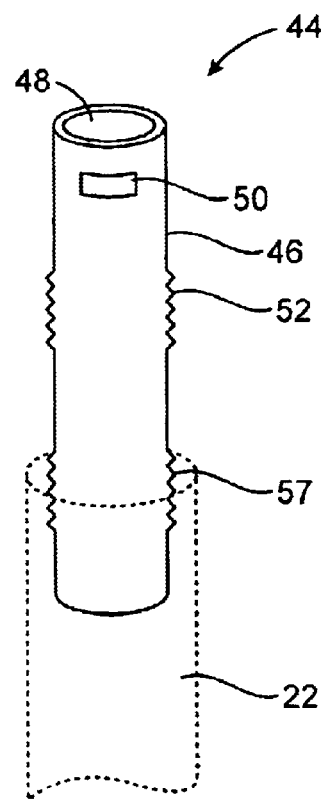
FIG. 7 is simplified view of a quick connect that couples the connector to the fluid conduit.

As shown in FIGS. 6 and 7, fluid conduit 22 can be coupled to the connector 20 with a hose quick connect 44. In the illustrated embodiment, a first end of the hose quick connect includes a first end 46 having an end opening 48 and a plurality of radial openings 50. The hose quick connect 44 can include threads 52 that engage corresponding threads 54 (FIG. 6) in housing 26 of connector so as to removably attach the fluid conduit 22 to the connector 20. A second end 47 of the hose quick connect 44 can include serrations or threads 57 or other connection means to grip and attach the fluid conduit to the quick connect 44.

As shown by the dotted line water flow in FIG. 6, during douching, when the fluid conduit is coupled to the connector, the fluid conduit 22 will push valve 36 off of seat 38 so as to allow water to flow around valve 36 into radial openings 50 and through the holes 42 in the wafer valve 36. Such a configuration provides for an increased water flow through outlet port 32 and into fluid conduit 22. If the user desires only to douche, the user can tighten connector 20 and push the connector tightly against shower head 12 to stop the flow of water between the connector 20 and shower head so as to direct substantially all of the water through fluid conduit 22.

Referring again to FIG. 3, when the quick connect 44 and fluid conduit 22 are removed from connector 20, valve 36 will be forced by the water pressure into contact with seat 38 so as to seal off the flow of water around the valve and the water will only be allowed to flow through the holes 42 so as to create a fluid flow for showering (FIG. 3). As noted above, if the connector is not tightly coupled to shower head 12, water may also flow around between connector 20 and shower head 12.

Fluid conduits 22 of the present invention can be composed of a variety of materials, such as rubber, vinyl, extruded rubber, or any other flexible tubing for delivering a fluid flow. Fluid conduit can be of any size that provides an acceptable flow to the user. Typically, however, fluid conduit 22 will have an inner diameter between approximately 5/16 inches and 7/16 inches and have a length between approximately 8 feet and 15 feet. It should be appreciated however that such dimensions can vary depending on the shower head arrangement, water flow, and the like.

Connector 20 can be fixedly or removably attached to the fluid conduit. In exemplary embodiments connector 20 is removably attached to fluid conduit 22 such that the connector 20 can be left on the shower rose 12 and the conduit 22 and applicator 24 can be removed and stored when not needed. In such embodiments, connector 20 can be configured to allow water to flow through apertures 42 in the check valve 36. Conduit 22 should not have a smaller inside diameter than 5/16 inches or during low water pressure the 25 psi to 35 psi douche time would be increased.

It should be appreciated that while the illustrated connector is threadedly attached, connector 20 and fluid conduit 22 can also be adhesively attached, snap fit, pressure fit, taper fit, or the like.

Figure 8:
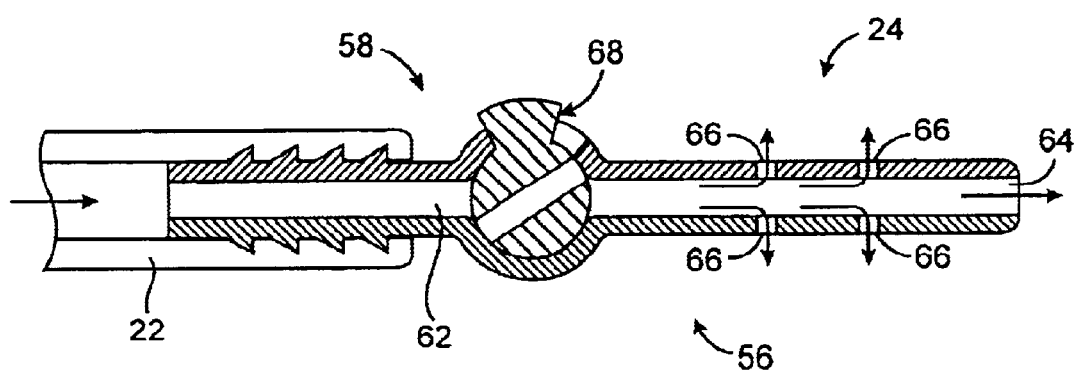
FIG. 8 is a cross sectional view of an exemplary applicator of the present invention having a valve.

FIG. 8 illustrates an exemplary applicator 24 of the present invention. Applicator can be directly attached to fluid conduit 22 or it can be attached to the fluid conduit via a reservoir, or other coupling mechanism. Applicator is typically comprised of an elongate body 56 having a proximal portion 58 that is attachable to the fluid conduit 22 and a distal portion 60 that is sized and shaped for insertion into the body orifice. Applicator can further include an inner lumen 62 for delivering the fluid flow to the desired target area. Applicator will typically have at least a distal opening 64 and may optionally also have radial openings 66 so as to deliver a fluid flow distally and radially within the body orifice. In the illustrated embodiment, the distal portion has a smaller diameter than the proximal portion so as to allow easier advancement into the body orifice.

As noted above, the applicators of the present invention can have a variety of sizes. For example, under normal conditions an applicator having a 1/4 inch inner diameter provides a sufficient flow rate for comfortable douching. It should be appreciated however, that in order to change the flow rate the user need only stop the flow at the applicator, alter the flow at the shower head, or at the faucet. As long as the fluid conduit has an inside diameter that is larger than the inside diameter of the applicator, flow will not be appreciably restricted.

Systems 10 of the present invention may optionally include a valve 68 for controlling the flow of fluid and/or a reservoir applicator assembly 69 (FIG. 9) for storing a liquid douching agent 70. Valve 68 of the present invention is preferably actuatable using a single hand so as to allow the user to easily control the applicator and flow of liquid to the desired target area. Valve 68 can be any conventional valve for controlling the flow of liquid, however, some preferred valves are t-valves, ball valves, or the like.

Figure 9:
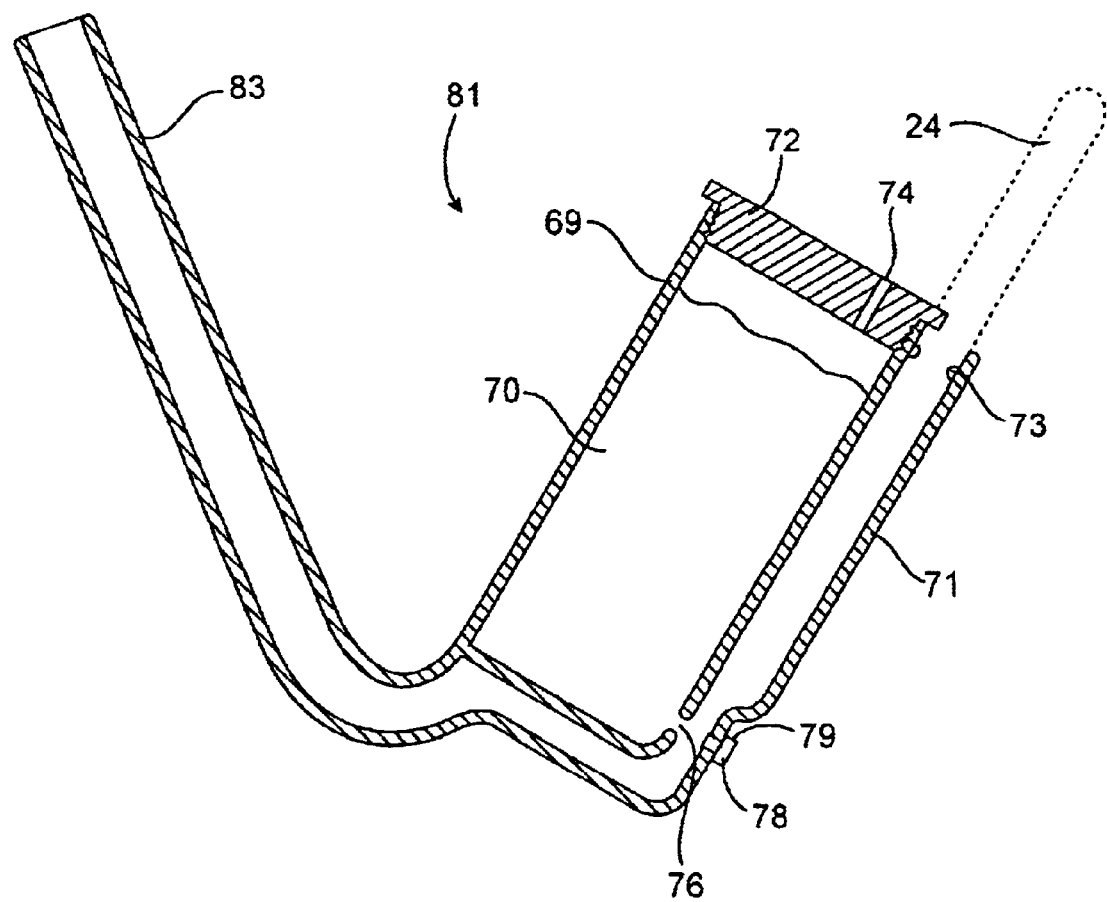
FIG. 9 shows a cross sectional view of an exemplary reservoir assembly attaching the fluid conduit and the applicator.

As seen in FIG. 9, reservoir assembly 81 includes a reservoir 69 and a coupling device 71 having an O-ring seal 73 for sealingly contacting the applicator 24 (shown in dotted lines). Reservoir 69 is in fluid communication with both the applicator 24 and fluid conduit 22. Reservoir 69 typically includes a cap 72 that is threadedly attached to the reservoir 69. Cap 72 can include a vent 74 for inlet of atmosphere to allow for an even metering flow of douching agent into another applicator 83 of the reservoir assembly 81. It should be appreciated however, that in other embodiments, the reservoir 69 can be kept in a vacuum atmosphere, but such embodiments will typically have inaccurate metering of the douching solutions.

The reservoir 59 can be filled with fluid cleaning agents, douching agents, or the like. Some exemplary homeopathic douching mixtures include vinegar or a baking powder emulsified in a water solution. Such mixtures, or other conventional powder or liquid mixtures, are placed in reservoir 69 and the water flow is delivered through the fluid conduit 22. As the water flows through conduit 22, the venturi effect delivers the agent 70 into the fluid flow via an inlet 76. The reservoir assembly can include a plug 78 and a sized opening 79 to create the accurate flow of the agent 70 and water flow.

Figure 10:
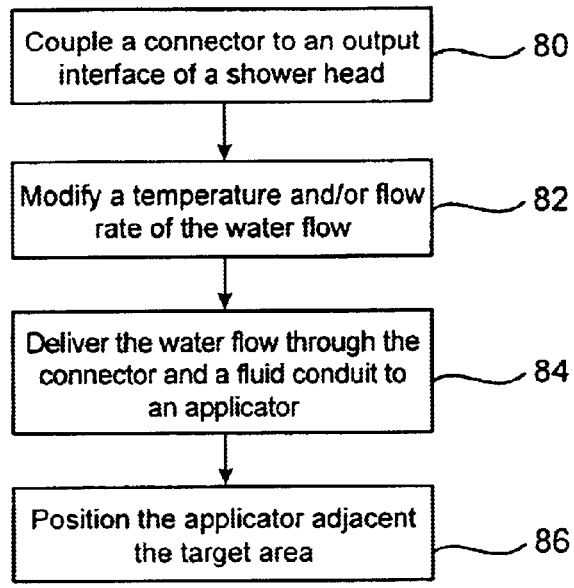
FIGS. 10 and 11 illustrate simplified methods of the present invention.
Figure 11:
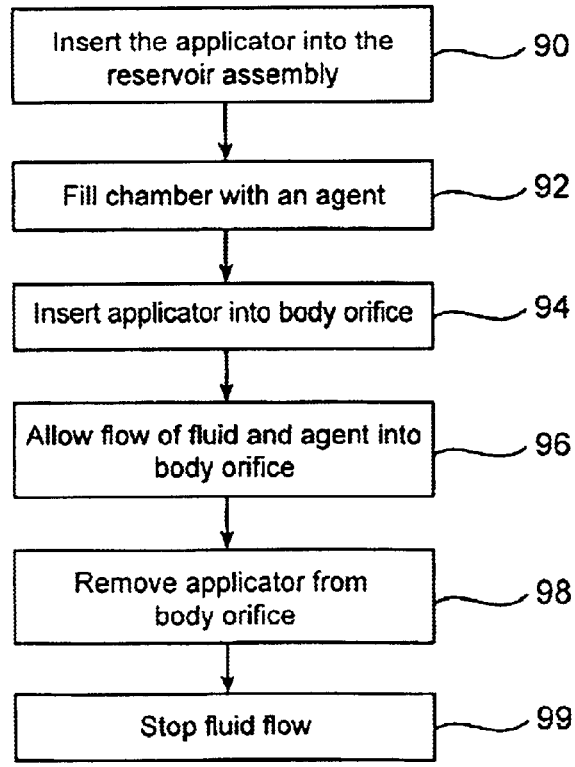

FIGS. 10 and 11 schematically illustrates some exemplary methods of the present invention. In a general sense, the connector can be coupled to an output interface of the shower head (Step 80). The water temperature and flow can be modified to a comfortable temperature (Step 82). Typically the temperature will be between 100° F. and 110° F. and the flow rate will typically be less than approximately 2.5 gallons per minute. Such a flow of hot water may be able to kill any sperm that is present in the vaginal canal and may dilute a sperm count below a potent level. The fluid will be delivered through the connector and fluid conduit to the applicator (Step 84). The user will position the applicator adjacent the target area and will let the fluid flow out of the applicator to douche (Step 86). Optionally, the user can either kink the fluid conduit or keep flow valve 56 in a closed position so as to stop the water flow out of the applicator.

As shown in FIG. 11, when the personal hygiene system includes a reservoir, the user can insert the applicator into the reservoir assembly (Step 90) and have the flow valve in a closed position or the fluid conduit kinked. The chamber can be filled with an emulsoid powder or fluid (Step 92) and the applicator can be inserted into the vagina (Step 94). The valve can be opened or the conduit unkinked so as to allow a flow of fluid and agent into the vagina (Step 96). When the reservoir is empty, the applicator can be removed from the vagina and the valve can be closed or the conduit kinked so as to stop the flow of fluid. (Steps 98, 99).

While the above is a complete description of the preferred embodiments of the inventions, various alternatives, modifications, and equivalents may be used. For example, it should be appreciated that instead of a valve adjacent the applicator to control the flow, the user may just kink the fluid conduit or applicator to stop the flow of water into the target area. Moreover, instead of forcing the fluid to flow through fluid inlets 33, 34, it may be possible to create a lumen in threaded shaft 30 so as to allow the water to flow through the threaded shaft and into the passageway 28.

Figure 12:
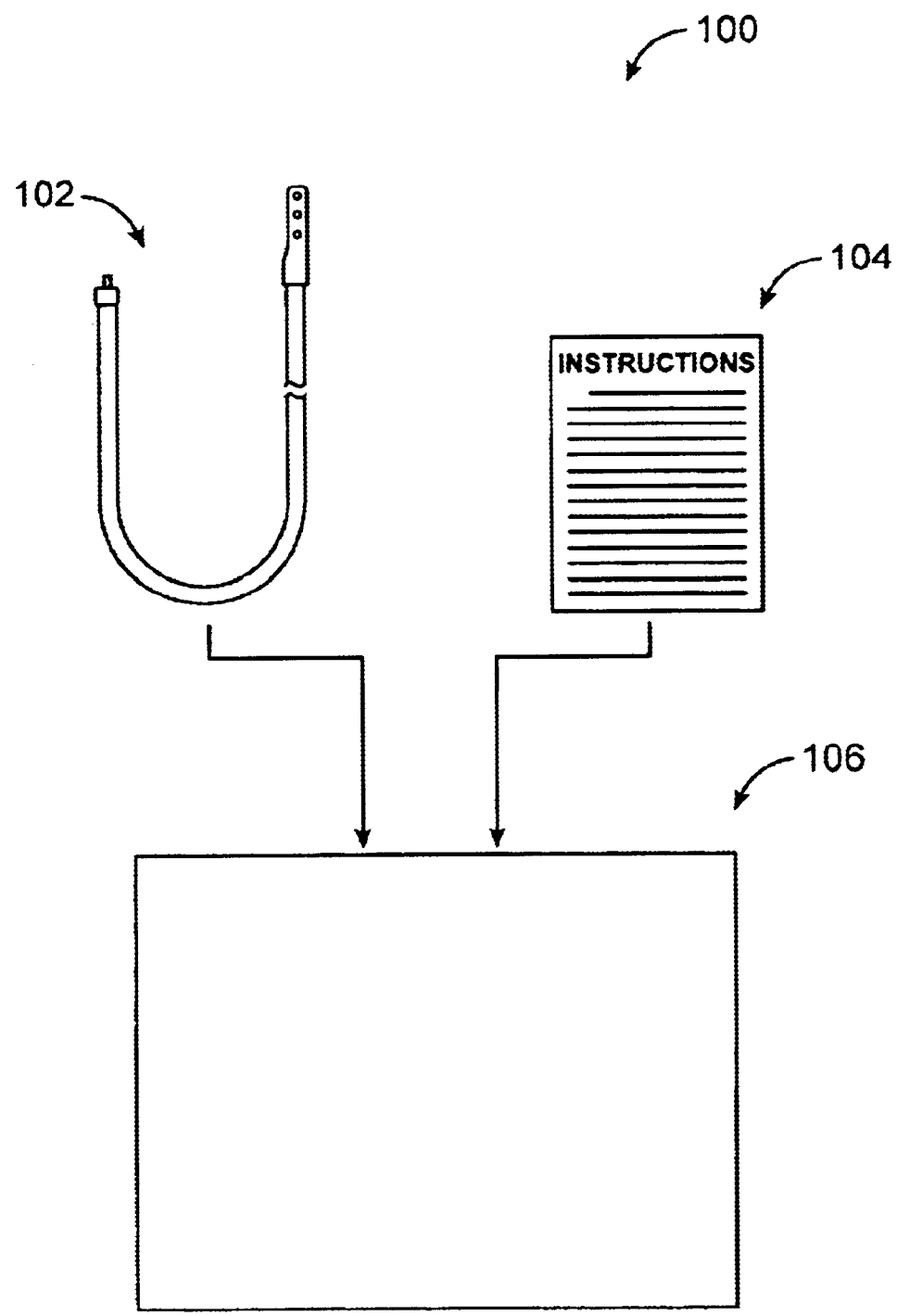
FIG. 12 illustrates a simplified kit of the present invention.

FIG. 12 illustrates an exemplary kit of the present invention. Kits 100 of the present invention typically include a douching system 102, instructions for use 104, and a package 106. The douching systems 102 can include a connector, a fluid conduit, and an applicator. Optionally, the douching system 102 can include a powder or liquid cleaning agent and/or a reservoir (not shown), as described above. The kit 100 typically includes instructions for use which describe any of the methods as described above. Package 106 may be any conventional packaging, including pouches, trays, boxes, tubes, or the like. The instructions for use 104 will usually be printed on a separate piece of paper, but may also be printed in whole or in part on a portion of the packaging 106, or in other conventional mediums.

Although the foregoing has been described in detail for purposes of clarity of understanding, it will be obvious that certain modifications may be practiced within the scope of the appended claims.

What is claimed is:

1. A personal hygiene system that is attachable to a shower head, the shower head comprising an input interface for receiving a fluid flow from a water source and an output interface for delivering the fluid flow to the user, the personal hygiene system comprising:

a connector housing comprising an inlet, an outlet, and a passageway extending therebetween, wherein the connector inlet is configured to receive a fluid flow directly from the output interface of the shower head and is configured to deliver the fluid into the passageway;

wherein the inlet comprises a threaded shaft for threadedly connecting the connector housing to the output interface of the shower head;

a valve positioned within the passageway of the connector housing and movable between a first position and a second position, the valve comprising at least one aperture to allow the flow of fluid out of the outlet of the connector housing;

a valve seat positioned within the passageway to position the valve within the passageway when the valve is in the first position;

an attachment device comprising a first open end and a second open end, wherein the fist open end further comprises at least one radial opening, wherein the first open end is attachable to the outlet of the connector housing for receiving the flow of fluid so as to move the valve to the second position to allow fluid to flow around the valve and into the at least one radial opening;

a flexible fluid conduit having a proximal end and a distal end, wherein the proximal end is coupled to the second open end of the attachment device to receive the fluid flow from the shower head; and an applicator coupled to the distal end of the fluid conduit for directing the fluid flow to a target area.

2. The personal hygiene system of claim 1, wherein the attachment device is removably attachable to the connector housing.

3. The personal hygiene system of claim 1 wherein removal of the attachment device allows fluid flow to exit the outlet of the housing only through the at least one aperture in the valve.

4. The personal hygiene system of claim 1 wherein the connector housing is removably attachable to the shower head with the threaded shaft.

5. The personal hygiene system of claim 1 wherein the fluid conduit is threadedly, adhesively, snap fit, pressure fit, or taper fit to the attachment device.

6. The personal hygiene system of claim 1 further comprising a detachable reservoir connected to one of the connector, fluid conduit, and applicator.

7. The personal hygiene system of claim 1 wherein the valve comprises a contoured wafer valve comprising a plurality of openings for regulating flow of the fluid through the fluid conduit.

8. The personal hygiene system of claim 7 wherein the applicator comprises an end opening and radial openings.

9. The personal hygiene system of claim 1 wherein the applicator is coupled to the flexible fluid conduit through a reservoir.

10. A personal douching system that is removably attachable to a shower head, the system comprising:

a connector having a threaded shaft, wherein the threaded shaft can be threadedly coupled to an output interface of the shower head, wherein the connector comprises:

a housing comprising an inlet, an internal cavity, and an outlet, wherein the inlet is attachable to the shower head to receive water flow from the shower head and to direct the water flow to the internal cavity; and a valve seat disposed within the internal cavity; and a contoured wafer valve comprising a plurality of openings positioned within the internal cavity to control the water flow through the connector;

a fluid conduit comprising a first end and a second end, wherein the first end is threadedly couplable to the connector housing to move the contoured wafer valve off of the valve seat to allow water to flow around the contoured wafer valve, wherein the first end of the fluid conduit comprises at least one radial opening for receiving water that flows around the contoured wafer valve; and a chamber assembly comprising a chamber to hold an agent for delivery into the water flow, wherein the second end of the fluid conduit is in communication with the chamber.

11. The system of claim 10 comprising an applicator in fluid communication with the second end of the fluid conduit to deliver the water flow and agent into a patient's target area.

12. The system of claim 10 wherein the chamber assembly is a venturi siphon chamber.

* * * * *